United States Patent [19]

Strekopytov et al.

[11] Patent Number: 4,615,474

[45] Date of Patent: Oct. 7, 1986

[54] INSTRUMENT FOR LIGATING BONE TISSUES OF RIBS AND CLAVICLES WITH METAL STAPLES

[75] Inventors: Alexei A. Strekopytov; Vladimir A. Sokolov; Alexandr P. Kuzmichev; Vladimir A. Strekopytov, all of Moscow, U.S.S.R.

[73] Assignee: Vsesojuzny Nauchno-Issledovatelsky I Ispytatelny Institut Meditsinskoi Tekhniki, Moscow, U.S.S.R.

[21] Appl. No.: 622,146

[22] Filed: Jun. 19, 1984

[51] Int. Cl.$^4$ ............................................. A61B 17/04
[52] U.S. Cl. ................................. 227/19; 128/334 R
[58] Field of Search ............... 128/334 R, 334 C, 325; 227/DIG. 1, 19; 206/339, 340

[56] References Cited

U.S. PATENT DOCUMENTS 3,822,818 7/1974 Strekopytov et al. .

FOREIGN PATENT DOCUMENTS 2109604 12/1973 Fed. Rep. of Germany .
927936 6/1963 United Kingdom ............ 128/334 R

*Primary Examiner*—Michael H. Thaler
*Attorney, Agent, or Firm*—Fleit, Jacobson, Cohn & Price

[57] ABSTRACT

An instrument for ligating bone tissues of ribs and clavicles with metal staples includes an anvil body rigidly connected to a staple driving body which accommodates a staple pusher. The latter is mounted for reciprocation in relation to the anvil body. A hook with an anvil is mounted on the staple driving body for reciprocation in relation to the latter. The staple pusher and the hook are driven by relatively movable assemblies composed of a nut and a screw, as well as cams which translate longitudinal motion of the screws in relation to the anvil body into transverse motion of the staple pusher and the hook relative to the anvil body.

3 Claims, 5 Drawing Figures

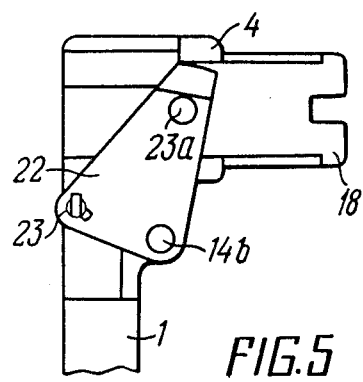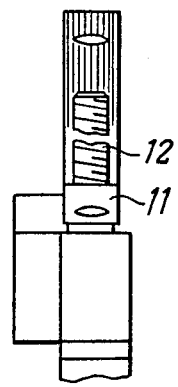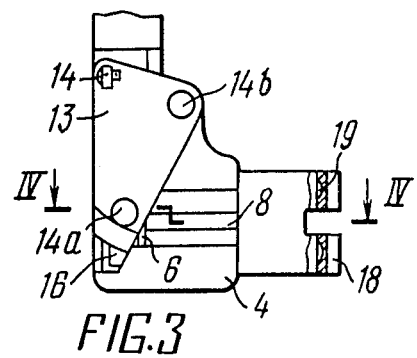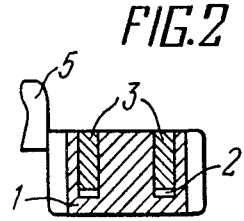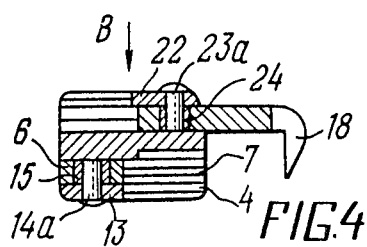

INSTRUMENT FOR LIGATING BONE TISSUES OF RIBS AND CLAVICLES WITH METAL STAPLES

FIELD OF THE INVENTION

The present invention relates to medical equipment and is more specifically concerned with instruments for ligating bone tissues of ribs and clavicles with metal staples.

BACKGROUND OF THE INVENTION

There is known an instrument for ligating bone tissues, which comprises an anvil body, a hook with an avil for bending the legs of staples, and a staple driving anvil which accommodates a staple pusher.

The hook is composed of two parts one of which is coupled to the anvil body, while the other is reciprocatable transversely to the anvil body. The second part of the hook is driven by a relatively movable assembly mounted on the anvil body and composed of a nut and a screw.

The staple driving body is hollow. It accommodates staples and is installed in guides provided on the anvil body.

The staple driving body is reciprocated along the anvil body by a relatively movable assembly composed of a nut and a screw, and the staple driving body moves along the anvil body toward the anvil of the hook.

The staple pusher is provided with a drive for pushing the staples out of the staple driving body so that the legs of the staples pierce the bone tissue and are brought into engagement with hollows provided in the anvil. In doing so, they are bent and ligate bone tissues (cf. FRG Pat. No. 2,109,604 and U.S. Pat. No. 3,822,818).

The instrument in question is intended for dealing with simple fractures of ribs, clavicles, jaws, etc.

In cases of multiple fractures of ribs, the use of this instrument for osteosynthesis requires multiple incisions of soft tissues of the thoracic wall in fractured areas. This prolongs the operation and makes it traumatic. In severe cases such operations may lead to extremely serious consequences. In dealing with rib fractures in the spinal part of the thoracic cage, it is necessary to dissect the broadest muscle of the back. The dissection results in total disability of that muscle and increases the total amount of blood lost during the operation.

SUMMARY OF THE INVENTION

It is an object of the present invention to provide an instrument for ligating bone tissues in cases of multiple fractures of one rib or fractures of several ribs from a single limited operative incision without further dissecting soft tissues.

The invention provides an instrument for ligating bone tissues of ribs and clavicles with metal staples, comprising an anvil body which carries a staple driving body accommodating a staple pusher mounted for reciprocation along the staple driving body, a hook with an anvil for bending the legs of staples, which is mounted for reciprocation in relation to the anvil body, and relatively movable assemblies composed of a nut and a screw for driving the staple pusher and the hook, which is characterized, according to the invention, in that the staple driving body is rigidly secured to the anvil body, and in that the staple pusher and the hook are arranged transversely to the anvil body and driven in that direction through cams which translate the longitudinal motion of the screw of the relatively movable assembly in relation to the anvil body into transverse motion of the staple pusher and the hook in relation to the anvil body.

It is preferred that the staple pusher and the hook be arranged at an angle of 90° to the anvil body. Such an arrangement is best from the viewpoint of the design.

It is also preferred that the staple pusher and the hook be coupled to the respective cams by means of sliders mounted on the cams and received in recesses provided in the staple pusher and the hook. This manner of coupling the staple pusher and the hook to the cams makes for a long service life of the instrument.

The instrument according to the invention for ligating bone tissues of ribs and clavicles is relatively simple in design, yet it is highly effective, for it makes it possible to ligate bone tissues in cases of multiple fractures of one rib or fractures of many ribs from a single limited incision without further dissecting soft tissues. The instrument of this invention is easy to manufacture and reliable in operation.

BRIEF DESCRIPTION OF THE ACCOMPANYING DRAWINGS

Other objects and advantages of the present invention will become more apparent from a consideration of the following detailed description of a preferred embodiment thereof, taken in conjunction with the accompanying drawings, wherein:

FIG. 2 is a section taken on line II—II in FIG. 1;

FIG. 3 is a view taken in the direction of the arrow A in FIG. 1;

FIG. 4 is a section taken on line IV—IV in FIG. 3;

FIG. 5 is a view taken in the direction of the arrow B in FIG. 4.

DETAILED DESCRIPTION OF THE INVENTION

Figure 1:
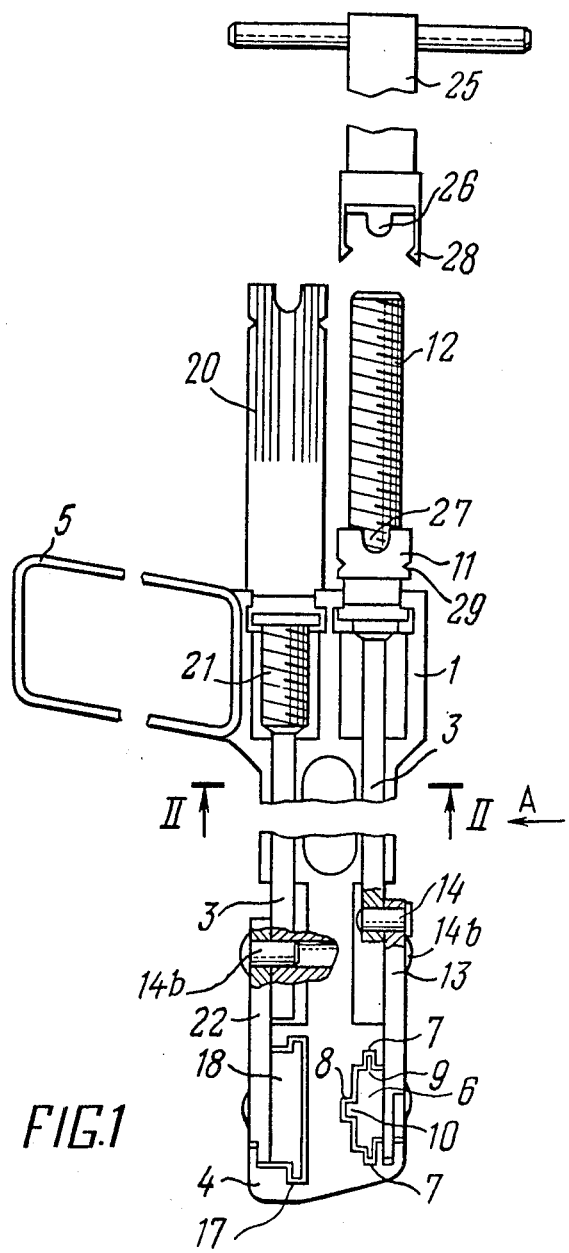
FIG. 1 is a general cut-away plan view of an instrument in accordance with the invention for ligating bone tissues.

With continued reference to the attached drawings, there is shown an instrument for ligating bone tissues of ribs and clavicles, which comprises an anvil body 1 (FIG. 1) formed with grooves 2 (FIG. 2) adapted to receive tie rods 3. Mounted on one end of the anvil body 1 is a staple driving body 4 (FIG. 1) which serves to accommodate U-shaped metal staples (not shown). In the embodiment under review, the staple driving body 4 is integral with the anvil body 1. A handle 5 is secured at the opposite end of the anvil body 1. The staple driving body 4 accommodates a staple pusher 6 which is mounted for reciprocation along the staple driving body 4. To this end, grooves 7 and 8 are provided in the side walls and the bottom of the staple driving body 4, and projections 9 and 10 are provided on the stapler pusher 6 to be received in the grooves 7 and 8, respectively. The grooves 7 and 8 extend transversely to the anvil body 1 and serve as guides for the staple pusher 6.

The staple pusher 6 is driven by a first relatively movable assembly composed of a nut 11 and a screw 12, and also a cam 13. The nut 11 and screw 12 are mounted on the anvil body 1.

The longitudinal motion of the screw 12 of the first relatively movable assembly in relation to the anvil body 1 is translated by the cam 13 into transverse motion of the pusher 6.

The cam 13 is coupled to the screw 12 through the tie rod 3 by means of an axle 14 (FIG. 1). The tie rod 3 (FIG. 1) is rigidly coupled to the screw 12 and received in the groove 2 (FIG. 2) of the anvil body 1.

The cam 13 (FIG. 3) is coupled to the pusher 6 through a slider 15 (FIG. 4). The latter is fitted on an axle 14a and received in a groove 16 (FIG. 3) provided in the pusher 6. The axle 14a is mounted on the cam 13.

The longitudinal side of the groove 16 is perpendicular to the direction of motion of the pusher 6. Such a coupling between the cam 13 and the pusher 6 provides for a long service life of the ligating instrument. The cam 13 is coupled to the anvil body 1 by means of an axle 14b.

On the side opposite to the pusher 6, the staple driving body 4 has guides 17 (FIG. 1) for a hook 18. An anvil 19 (FIG. 3) with hollows for bending the legs of staples is provided on the hook 18, which is mounted for reciprocation in the same direction as the staple pusher 6 and is intended to compress the ribs being ligated between the end face of the staple driving body 4 and the anvil 19.

The hook 18 is driven by a second relatively movable assembly composed of a nut 20 and a screw 21, as well as a cam 22. The second relatively movable assembly is mounted on the anvil body 1. The cam 22 translates longitudinal motion of the screw 21 into transverse motion of the hook 18 relative to the anvil body 1. The cam 22 is coupled to the screw 21 through the tie rod 3 which is rigidly connected to the screw 21 and coupled to the cam 22 by means of an axle 23. The cam 22 is coupled to the hook 18 through a slider 24 (FIG. 4) mounted on an axle 23a. The slider 24 is received in a groove provided in the hook 18, which is similar to the groove 16 in the pusher 6.

The axle 14b (FIG. 1) connects the cams 13 and 22 to the anvil body 1.

In the embodiment under review, the guides 7, 8 and 17 of the staple pusher 6 and the hook 18 with the anvil 19 extend in the staple driving body 4 at an angle of 90° to the anvil body 1.

The first relatively movable assembly composed of the nut 11 and screw 12 has a right-hand thread. The second relatively movable assembly composed of the nut 20 and screw 21 has a left-hand thread.

The nut 11 and, if necessary, the nut 20 are rotated by a wrench 25 having a projection 26 which is engaged with a groove 27 provided in the nut 11.

Spontaneous separation of the nut 11 and screw 12 is prevented by a spring 28 received in hollows 29 provided in the nut 11.

The instrument according to the invention for ligating bone tissues of ribs and clavicles operates as follows.

An incision of the skin and subcutaneous fat is made and the muscles of the thoracic wall are pulled to the sides so as to lay bare all the rib fractures. A U-shaped staple is inserted into the groove 7 of the staple driving body 4 so that its legs face the anvil 19. The muscles, subcutaneous fat and skin are lifted and the ligating instrument according to the invention, which is held by the handle, is introduced into the operative wound. The hook 18 is placed under the rib so that the fracture is between the anvil 19 of the hook 18 and the end face of the staple driving body 4.

The nut 20 is rotated to drive the tie rod 3 so that the cam 22 is rotated around the axle 14b. The slider 24 moves in the groove of the hook 18 and transmits motion to the hook 18 which is driven along the staple driving body 4 until the rib pieces being ligated are tightly held between the latter and the anvil 19. As the nut 11 is rotated, the screw 12 and tie rod 3 move along the anvil body 1, causing the cam 13 to rotate around the axle 14b. As this takes place, the slider 15 moves in the longitudinal groove 16 of the pusher 6 and drives the latter transversely to the anvil body 1. The staple pusher 6 moves the staple toward the rib. The staple must be positioned opposite the line of fracture. During further movement of the staple its legs pierce the rib pieces and then are brought into engagement with the hollows of the anvil and bent, whereupon they again pierce the bone tissue. By rotating the nut 20 in the opposite direction, the hook 18 and the anvil 19 are removed from the staple driving body 4.

The instrument is removed from under the ligated rib and from the operative wound.

What is claimed is:

1. An instrument for ligating bone tisues of ribs and clavicles with metal staples, comprising an anvil body; a staple driving body rigidly connected to said anvil body; a staple pusher mounted in said staple driving body for reciprocation transversely to said anvil body; a means for driving said staple pusher, comprising a first relatively movable assembly mounted on said anvil body and including a nut and a screw, a cam coupled to said staple pusher and to the screw of said first relatively movable assembly and pivotable about a fixed axle carried by said anvil body to translate the longitudinal motion of the screw relative to said anvil body into transverse motion of said pusher relative to said anvil body; a hook with an anvil for bending the legs of staples, mounted on said staple driving body so that it can move in relation to said staple driving body in order to produce a gap between said hook and an end face of said staple driving body, which gap is intended to accommodate bone tissues to be ligated; a means for driving said hook with said anvil, comprising a second relatively movable assembly mounted on said anvil body and including a nut and a screw, a cam coupled to said hook and to the screw of said second relatively movable assembly and pivotable about a fixed axle carried by said anvil body to translate the longitudinal motion of said screw in relation to said anvil body into transverse motion of said hook with said anvil in relation to said anvil body; and a handle secured to said anvil body.

2. An instrument as claimed in claim 1, wherein said staple pusher and said hook with said anvil are arranged at an angle of 90° to said anvil body.

3. An instrument as claimed in claim 1, wherein said staple pusher and said hook are coupled to the respective cams by means of sliders mounted on the cams and received in grooves provided in the staple pusher and the hook.

* * * * *